US009213406B2

United States Patent
Ou-Yang et al.

(10) Patent No.: US 9,213,406 B2
(45) Date of Patent: Dec. 15, 2015

(54) HEAD-MOUNT EYE TRACKING SYSTEM WITH IMPROVED DETERMINATION OF GAZING POSITION

(71) Applicant: National Chiao Tung University, Hsinchu (TW)

(72) Inventors: Mang Ou-Yang, Hsinchu (TW); Jin-Chern Chiou, Hsinchu (TW); Ting-Wei Huang, Hsinchu (TW); Chun-Cheng Hu, Hsinchu (TW); Jyun-Wei Jhuang, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 108 days.

(21) Appl. No.: 14/139,887

(22) Filed: Dec. 24, 2013

(65) Prior Publication Data

US 2015/0035745 A1    Feb. 5, 2015

(30) Foreign Application Priority Data

Jul. 30, 2013    (TW) .............................. 102127317 A

(51) Int. Cl.
*G06F 3/01* (2006.01)
*G02B 27/01* (2006.01)
*A61B 3/113* (2006.01)

(52) U.S. Cl.
CPC ................ *G06F 3/013* (2013.01); *A61B 3/113* (2013.01); *G02B 27/017* (2013.01); *G02B 2027/0138* (2013.01); *G02B 2027/0178* (2013.01); *G02B 2027/0187* (2013.01)

(58) Field of Classification Search
CPC .................. G06F 3/013; G02B 27/017; G02B 2027/0138; G02B 2027/0178; G02B 2027/0187; A61B 3/113
See application file for complete search history.

(56) References Cited

U.S. PATENT DOCUMENTS

| 4,145,122 A | 3/1979 | Rinard et al. |
| 5,345,281 A | 9/1994 | Taboada et al. |
| 2004/0196433 A1* | 10/2004 | Durnell ......................... 351/209 |
| 2013/0127980 A1* | 5/2013 | Haddick et al. ............ 348/14.08 |

FOREIGN PATENT DOCUMENTS

| CN | 201503524 | 6/2010 |
| TW | 299433 | 3/1997 |

OTHER PUBLICATIONS

Li et al., "openEyes: a low-cost head-mounted eye-tracking solution," Proceedings of the 2006 symposium on Eye tracking research & applications, Mar. 27-29, 2006, pp. 95-100.
"Office Action of Taiwan Counterpart Application", issued on Apr. 1, 2015, p. 1-p. 3.

* cited by examiner

*Primary Examiner* — Larry Sternbane
(74) *Attorney, Agent, or Firm* — Jianq Chyun IP Office

(57) ABSTRACT

A head-mount eye tracking system including a first light source, a first pupil image capturing device, a first and a second environmental image capturing devices, a fixing device and an image identification system. The first light source is applied to illuminate a first eye of a user. The first pupil image capturing device is applied to capture a first pupil image of the first eye. The first and the second environmental image capturing devices are respectively applied to capture a first and a second environmental images in front of the user. The fixing device is mounted to the head of the user to fix the first light source, the first pupil image capturing device, the first and the second environmental image capturing devices on the head of the user. The image identification system is applied to map the first or the second environmental images to the first pupil image.

6 Claims, 2 Drawing Sheets

HEAD-MOUNT EYE TRACKING SYSTEM WITH IMPROVED DETERMINATION OF GAZING POSITION

CROSS-REFERENCE TO RELATED APPLICATION

This application claims the priority benefit of Taiwan application serial no. 102127317, filed on Jul. 30, 2013. The entirety of the above-mentioned patent application is hereby incorporated by reference herein and made a part of this specification.

BACKGROUND

1. Technical Field

The invention relates to an eye tracking system. Particularly, the invention relates to a head-mount eye tracking system.

2. Related Art

Presently, an eye tracking technique is mainly divided into a contact eye tracking technique that requires contacting the eye and a non-contact eye tracking technique without contacting the eye. The contact eye tracking technique mainly includes a search-coil (SC) method and an electro-oculography (EOG) method, and the non-contact eye tracking technique mainly includes a free-head eye tracking technique and a head-mount eye tracking technique.

Regarding the contact eye tracking technique, taking the SC method as an example, a user is required to wear contact lenses having sensing coils. When the user rotates eyeballs to drive the lenses, the sensing coils produce an induced electromotive force (EMF) due to variation of a magnetic flux, and a magnitude of the EMF represents a deflection angle of the eyeball. Regarding the EOG method, a plurality of electrodes are attached around the eye, and the electrodes are used to detect a voltage difference generated by the eyeball rotation to determine the deflection angle of the eyeball. A disadvantage of the contact eye tracking technique is that contact of a foreign matter may cause strong eye discomfort, and eye and/or skin secretions may cause signal interference.

Regarding the free-head eye tracking technique, an eye tracker with a screen and dual image capturing devices is developed. However, the existing free-head eye tracking technique is still required to resolve a problem of errors caused by movement of user's head. Moreover, the free-head eye tracking technique also has disadvantages of complex in operation and high cost, etc.

Comparatively, regarding the head-mount eye tracking technique, an image capturing device and a light source are mounted on user's head, and a pupil image captured by the image capturing device is used to deduce a gazing position, which may eliminate the error caused by movement of the user's head. Therefore, the head-mount eye tracking system can be widely applied in industries of biomedicine, medical treatment, transportation and entertainment, etc. However, since the existing head-mount eye tracking technique determines the gazing position of the user only according to the eye information (the pupil image), it is easy to make a wrong determination. Moreover, the existing head-mount eye tracking technique generally has a problem that a sight line is shielded by the head-mount eye tracking system, which causes inconvenience in utilization.

SUMMARY

Accordingly, the invention is directed to a head-mount eye tracking system, which mitigates problems of wrong determination and shielding of a sight line.

The invention provides a head-mount eye tracking system including a first light source, a first pupil image capturing device, a first environmental image capturing device, a second environmental image capturing device, a fixing device and an image identification system. The first light source sends a first light beam to illuminate a first eye of a user. The first pupil image capturing device is disposed on a transmission path of the first light beam reflected by the first eye to capture a first pupil image of the first eye. The first environmental image capturing device is adapted to capture a first environmental image in front of the user. The second environmental image capturing device is adapted to capture a second environmental image in front of the user. The fixing device is disposed on the head of the user for fixing the first light source, the first pupil image capturing device, the first environmental image capturing device and the second environmental image capturing device on the head of the user. The image identification system is adapted to map at least one of the first environmental image and the second environmental image to the first pupil image, so as to determine a gazing position of the user.

In an embodiment of the invention, the first light source is selected from a visible-light light source or an invisible-light light source.

In an embodiment of the invention, the invisible-light light source is selected from an infrared light-emitting diode (IR LED), an ultraviolet light-emitting diode (UV LED) or laser.

In an embodiment of the invention, the first pupil image capturing device, the first environmental image capturing device and the second environmental image capturing device are respectively selected from a charge coupled device (CCD), a complementary metal-oxide semiconductor (CMOS) device or an infrared (IR) camera.

In an embodiment of the invention, the first pupil image capturing device, the first environmental image capturing device and the second environmental image capturing device respectively have a horizontal viewing angle and a vertical viewing angle, wherein the horizontal viewing angle is greater than 40 degrees and smaller than 180 degrees, and the vertical viewing angle is greater than 55 degrees and smaller than 180 degrees.

In an embodiment of the invention, the fixing device is a pair of glasses. The pair of glasses includes a glasses frame and two lenses fixed on the glasses frame. The glasses frame includes two lens frame portions, a first connection portion, two second connection portions and two ear hooking portions, wherein the first connection portion connects the two lens frame portions, each of the second connection portions connects the ear hooking portion with the adjacent lens frame portion, and the lenses are located in the lens frame portions. The first environmental image capturing device and the second environmental image capturing device are disposed on the first connection portion, and the first pupil image capturing device is disposed on the ear hooking portion adjacent to the first eye, and the first light source is disposed on one of the first connection portion, the second connection portion adjacent to the first eye and the ear hooking portion adjacent to the first eye.

In an embodiment of the invention, the head-mount eye tracking system further includes a second light source and a second pupil image capturing device. The second light source sends a second light beam to illuminate a second eye of the user. The second pupil image capturing device is disposed on a transmission path of the second beam reflected by the second eye to capture a second pupil image of the second eye, wherein the second light source and the second pupil image capturing device are fixed on the fixing device, and the image identification system is adapted to map at least one of the first environmental image and the second environmental image to the second pupil image.

In an embodiment of the invention, the head-mount eye tracking system further includes a data storage system and a transmission element. The data storage system is adapted to store the first pupil image, the first environmental image and the second environmental image, or store the gazing position of the user that is identified by the image identification system. The gazing position of the user that is identified by the image identification system or the first pupil image, the first environmental image and the second environmental image are transmitted to the data storage system through the transmission element.

In an embodiment of the invention, the first pupil image capturing device, the first environmental image capturing device and the second environmental image capturing device respectively have a horizontal viewing angle and a vertical viewing angle, wherein the horizontal viewing angle is greater than 20 degrees and smaller than 180 degrees, and the vertical viewing angle is greater than 20 degrees and smaller than 180 degrees.

According to the above descriptions, in the head-mount eye tracking system of the invention, by configuring the environmental image capturing devices and the pupil image capturing devices to capture the environmental images in front of the user and the pupil images of the eyes, and by mapping the environmental image to the pupil image, the problem of wrong determination is mitigated. Moreover, by configuring two environmental image capturing devices, the head-mount eye tracking system of the invention may further obtain distance information (i.e. a distance of an object) between the object in the environment and the user, so as to improve determination accuracy. Moreover, the head-mount tracking system of the invention fixes the light source and the image capturing device around the eye of the user instead of disposing the same in front of the user, so as to mitigate the problem of shielding a sight line.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF DISCLOSED EMBODIMENTS

Figure 1:
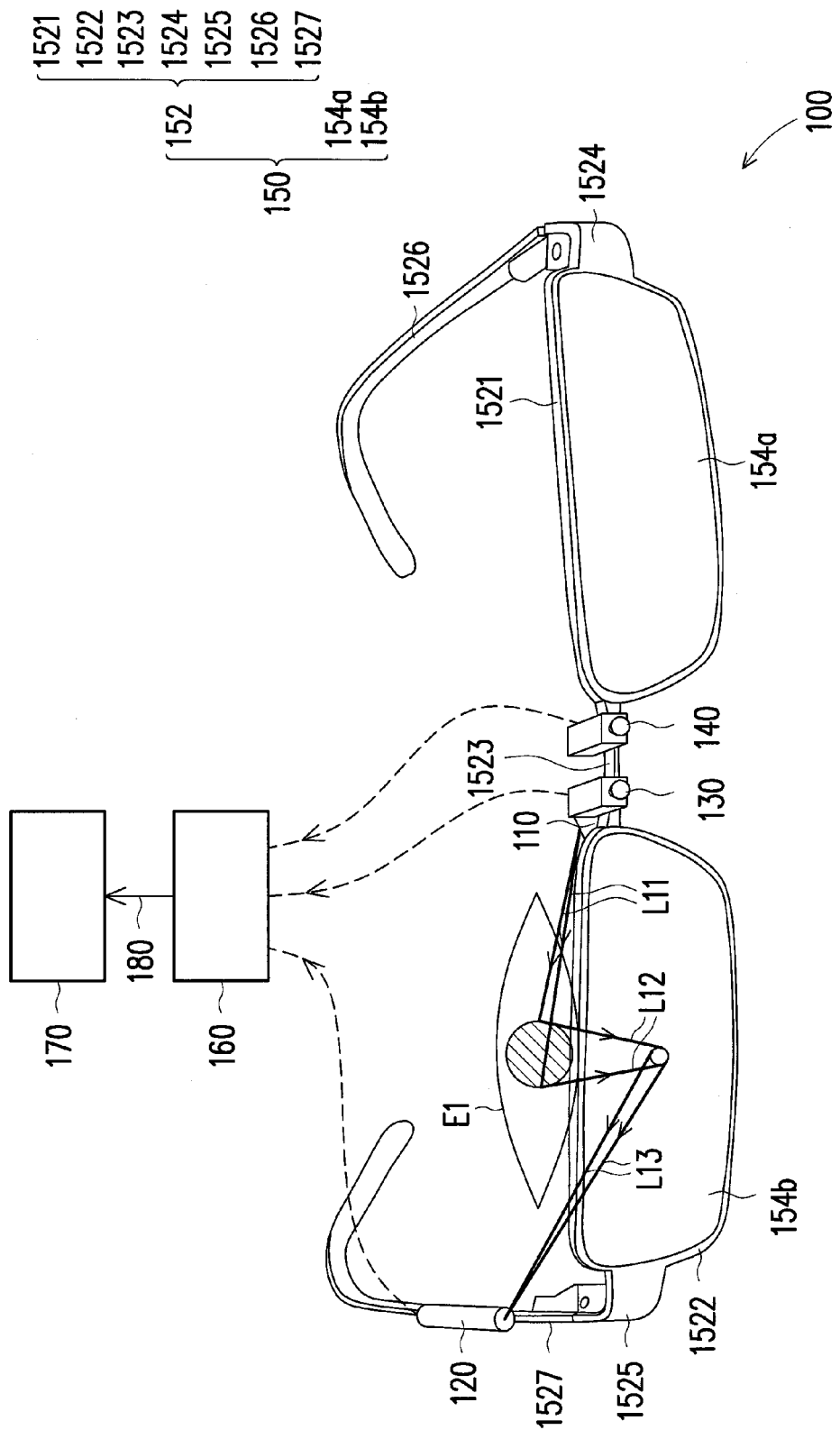
FIG. 1 is a side view of a head-mount eye tracking system according to a first embodiment of the invention.

FIG. 1 is a side view of a head-mount eye tracking system according to a first embodiment of the invention. Referring to FIG. 1, the head-mount eye tracking system 100 includes a first light source 110, a first pupil image capturing device 120, a first environmental image capturing device 130, a second environmental image capturing device 140, a fixing device 150 and an image identification system 160, wherein the fixing device 150 is suitable to be mounted on the head of a user (not shown), so as to fix the first light source 110, the first pupil image capturing device 120, the first environmental image capturing device 130 and the second environmental image capturing device 140 around a first eye E1 of the user.

The fixing device 150 can be a pair of glasses, a headcloth, a hat or a cap, etc. that is suitable for fixing the above elements on the head and is suitable for being removed from the head, so as to achieve better flexibility and convenience. In the present embodiment, the fixing device 150 is, for example, a pair of glasses. In detail, the pair of glasses, for example, includes a glasses frame 152 and two lenses 154a and 154b fixed on the glasses frame 152. Further, the glasses frame 152 includes two lens frame portions 1521 and 1522, a first connection portion 1523, two second connection portions 1524 and 1525 and two ear hooking portions 1526 and 1527, wherein the first connection portion 1523 connects the two lens frame portions 1521 and 1522, and each of the second connection portions 1524 and 1525 connects the ear hooking portion 1526, 1527 with the adjacent lens frame portion 1521, 1522. In detail, the second connection portion 1524 connects the ear hooking portion 1526 with the adjacent lens frame portion 1521, and the second connection portion 1525 connects the ear hooking portion 1527 with the adjacent lens frame portion 1522. Moreover, the lenses 154a and 154b are located in the lens frame portions 1521 and 1522.

In the present embodiment, the first environmental image capturing device 130 and the second environmental image capturing device 140 are, for example, disposed on the first connection portion 1523, the first pupil image capturing device 120 is, for example, disposed on the ear hooking portion 1527 adjacent to the first eye E1, and the first light source 110 is, for example, disposed on the first connection portion 1523 on a surface opposite to that of the first environmental image capturing device 130 and the second environmental image capturing device 140. However, a configuration relationship of the first light source 110, the first pupil image capturing device 120, the first environmental image capturing device 130 and the second environmental image capturing device 140 can be determined according to an actual design requirement. For example, in other embodiments, the first light source 110 can also be disposed on the second connection portion 1525 adjacent to the first eye E1, or disposed on the ear hooking portion 1527 adjacent to the first eye E1. Namely, the first light source 110 can be disposed on one of the first connection portion 1523, the second connection portion 1525 adjacent to the first eye E1 and the ear hooking portion 1527 adjacent to the first eye E1.

The first light source 110 is adapted to illuminate the first eye E1 of the user, such that the first pupil image capturing device 120 can capture a first pupil image of the first eye E1. In detail, by configuring the first light source 110, a situation that external light intensity influences the first pupil image captured by the first pupil image capturing device 120 is mitigated. The first light source 110 sends a first light beam L11 to illuminate the first eye E1 of the user, and the first pupil image capturing device 120 can capture the first pupil image of the first eye E1 in case of inadequate external light (for example, cloudy day, at night or in theatre, etc.).

The first light source 110 is selected from a visible-light light source or an invisible-light light source, wherein the visible-light light source is, for example, a light-emitting diode (LED) with a wavelength under a visible-light range (for example, a wavelength greater than 400 nm and smaller than 700 nm), and the invisible-light light source is, for example, an infrared light-emitting diode (IR LED), an ultraviolet light-emitting diode (UV LED) or laser with low power. Particularly, when the invisible-light light source is used as the first light source 110, visibility of the first light beam L11 sent by the first light source 110 is decreased. Moreover, when the first light source 110 adopts the IR LED, by forming an IR filter on a surface of the lens 154b adjacent to the user, a contrast of the first pupil image received by the first pupil image capturing device 120 is further improved.

The first pupil image capturing device 120 is applied for capturing the first pupil image of the first eye E1 and is, for example, disposed at a position that is suitable for directly or indirectly capture the first pupil image. For example, the first pupil image capturing device 120 can be disposed on the second connection portion 1525 or the first connection portion 1523 and face the first eye E1. Alternatively, as shown in FIG. 1, the first pupil image capturing device 120 can also be disposed on a transmission path of the first light beam L12 reflected by the first eye E1 for capturing the first pupil image of the first eye E1. In the present embodiment, the first light beam L12 reflected by the first eye E1 is, for example, reflected at least once by the lens 154b and is transmitted to the first pupil image capturing device 120. Namely, the first pupil image capturing device 120 is, for example, disposed on a transmission path of the first light beam L13 reflected by the lens 154b. Since the first pupil image capturing device 120 is fixed around the first eye E1 of the user (for example, fixed on the ear hooking portion 1527) instead of disposing the same in front of the user, the problem of shielding a sight line is mitigated. Moreover, by transmitting the first pupil image to the first pupil image capturing device 120 through reflection of the lens 154b, an angle that the first pupil image is obliquely incident to the first pupil image capturing device 120 is decreased, so as to decrease a calibration error and improve a resolution.

The first pupil image capturing device 120 can be a charge-coupled device, a complementary metal oxide semiconductor device or an IR camera, wherein the first pupil image capturing device 120 has a horizontal viewing angle and a vertical viewing angle. Since a field of vision of human eye is rather broad, in order to accurately obtain the first pupil image of the first eye E1, the horizontal viewing angle of the first pupil image capturing device 120 of the present embodiment is greater than 20 degrees and smaller than 180 degrees, and the vertical viewing angle is greater than 20 degrees and smaller than 180 degrees. In a preferred embodiment, the horizontal viewing angle of the first pupil image capturing device 120 is greater than 40 degrees and smaller than 180 degrees, and the vertical viewing angle is greater than 55 degrees and smaller than 180 degrees.

The first environmental image capturing device 130 is adapted to capture a first environmental image in front of the user, and the second environmental image capturing device 140 is adapted to capture a second environmental image in front of the user. For example, the first environmental image capturing device 130 and the second environmental image capturing device 140 can be respectively a charge-coupled device, a complementary metal oxide semiconductor device or an IR camera.

In the present embodiment, the first environmental image is different to the second environmental image. In detail, the first environmental image and the second environmental image are, for example, respectively environmental images in front of the user that are synchronously captured by the first environmental image capturing device 130 and the second environmental image capturing device 140. However, by adjusting a configuration relationship of the first environmental image capturing device 130 and the second environmental image capturing device 140, although the first environmental image and the second environmental image are image frames obtained by capturing a same object, the first and second environmental images have a viewing angle difference. In this way, distance information (a distance between the object and the user) of the object in front of the user can be obtained through image processing, so as to improve accuracy of determining a gazing position of the user.

The first environmental image capturing device 130 and the second environmental image capturing device 140 respectively have a horizontal viewing angle and a vertical viewing angle. In order to preferably map the first environmental image captured by the first environmental image capturing device 130 and the second environmental image captured by the second environmental image capturing device 140 to the first pupil image, the horizontal viewing angle of the first environmental image capturing device 130 and the second environmental image capturing device 140 is preferably greater than 20 degrees and smaller than 180 degrees, and the vertical viewing angle thereof is preferably greater than 20 degrees and smaller than 180 degrees. In a preferred embodiment, the horizontal viewing angle of the first pupil image capturing device 120 is greater than 40 degrees and smaller than 180 degrees, and the vertical viewing angle is greater than 55 degrees and smaller than 180 degrees.

In the present embodiment, the first pupil image, the first environmental image and the second environmental image can be respectively transmitted to the image identification system 160 through a wired or wireless transmission manner. The image identification system 160 is adapted to map at least one of the first environmental image and the second environmental image to the first pupil image, so as to determine the gazing position of the user, wherein the image identification system 160 can be an embedded system, for example, a chip integrated to a mobile device. Alternatively, the image identification system 160 can also be an independent system, which determines the gazing position of the user through an operating system.

Moreover, the head-mount eye tracking system 100 may further include a data storage system 170 and a transmission element 180, wherein the data storage system 170 is adapted to store the first pupil image, the first environmental image and the second environmental image, or store the gazing position of the user that is identified by the image identification system 160. For example, when the image identification system 160 adopts an embedded system, the data storage system 170 can be integrated to the embedded system, and can only store the gazing position of the user that is identified by the image identification system 160, so as to save a storage space of the data storage system 170. Alternatively, the data storage system 170 can be a cloud hard drive, a flash drive or a hard drive, and the gazing position of the user that is identified by the image identification system 160 or the first pupil image, the first environmental image and the second environmental image can be transmitted to the data storage system 170 through the transmission element 180 (for example, a wireless or wired transmission element). In other words, the transmission element 180 can be a wireless or wired transmission element according to a type of the data storage system 170. For example, the wireless transmission element is, for example, a Bluetooth transmission.

The head-mount eye tracking system 100 tracks the eye (the first eye E1) through a non-invasive manner (i.e. the head-mount eye tracking system 100 does not directly contact the eye), and the first and the second environmental image capturing devices 130 and 140 are used to capture the environmental images in front of the user, and the image identification system 160 is used to map at least one of the first environmental image and the second environmental image to the first pupil image, so as to identify the gazing position of the user. Since the head-mount eye tracking system 100 of the present embodiment can mitigate problems of wrong determination and shielding of the sight line, and can improve determination accuracy by obtaining distance information between the user and the object in the environment (i.e. a distance of the object), the head-mount eye tracking system 100 of the present embodiment has a broad application range. For example, when the head-mount eye tracking system 100 of the present embodiment is used in collaboration with computer mouse operation, a convenient eye tracking and controlling system is provided to people with disabilities or people with inconvenient hands. On the other hand, the head-mount eye tracking system 100 of the present embodiment can also objectively analyze consumer psychology and market trends or provide driving warnings by identifying eye tracks. Moreover, by combining brain wave measurement, the head-mount eye tracking system 100 of the present embodiment can further determine an influence of user's physical or mental illness on the eye track or concentration.

It should be noticed that in the aforementioned embodiment, only the environmental image is mapped to the pupil image of a single eye, though the invention is not limited thereto. In the following embodiment of FIG. 2, an implementation of mapping the environmental images to the pupil images of two eyes is described below.

Figure 2:
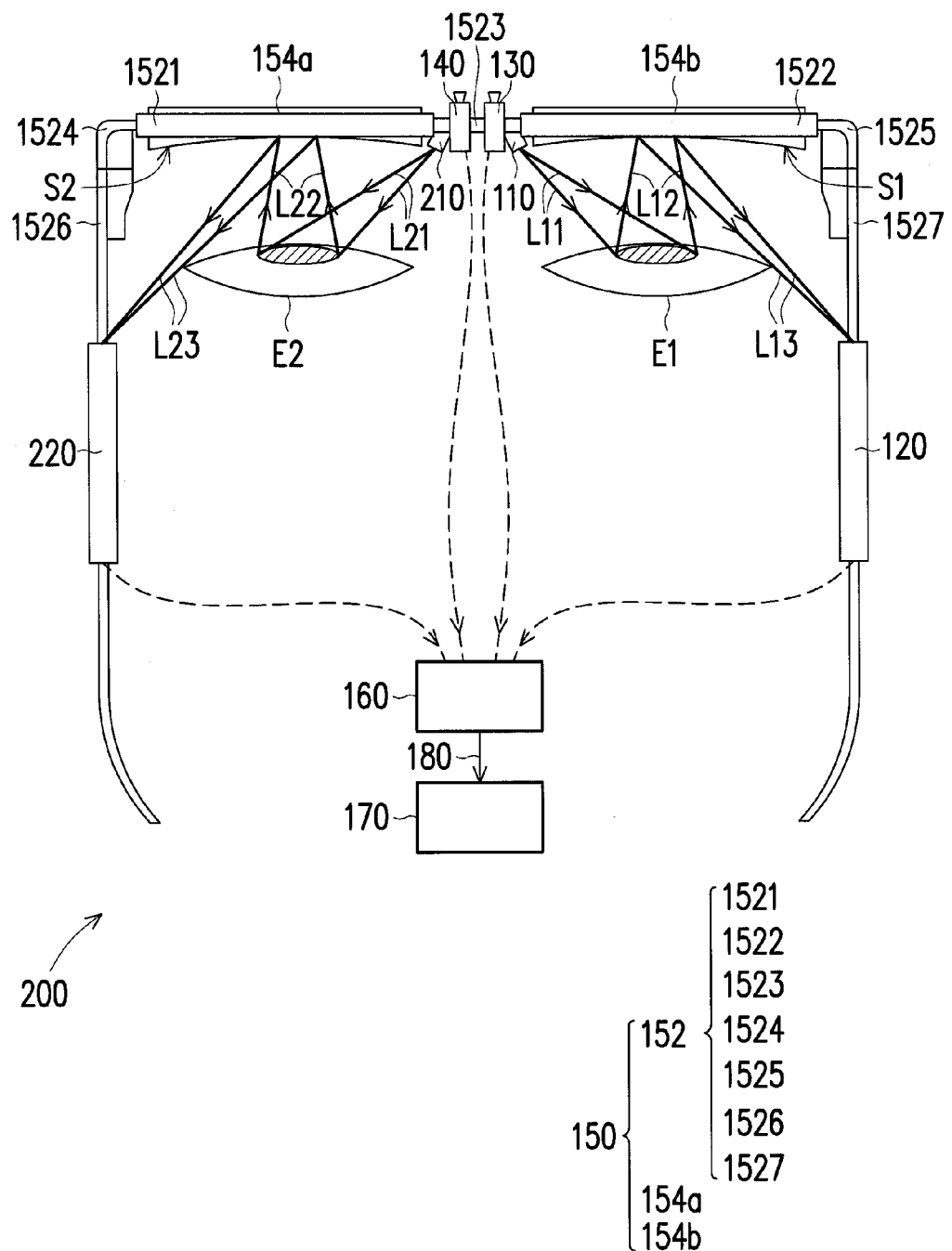
FIG. 2 is a top view of a head-mount eye tracking system according to a second embodiment of the invention.

FIG. 2 is a top view of a head-mount eye tracking system according to a second embodiment of the invention. Referring to FIG. 2, the head-mount eye tracking system 200 of the present embodiment has similar elements, effects and application range with that of the head-mount eye tracking system 100 of FIG. 1. A main difference therebetween is that the head-mount eye tracking system 200 of the present embodiment further includes a second light source 210 and a second pupil image capturing device 220. Moreover, the second light source 210 and the second pupil image capturing device 220 are fixed on the fixing device 150. In the present embodiment, the fixing device 150 fixes the second light source 210 and the second pupil image capturing device 220 around the second eye E2, but the invention is not limited thereto.

In the present embodiment, the second light source 210 is, for example, disposed on the first connection portion 1523, and the second pupil image capturing device 220 is, for example, disposed on the ear hooking portion 1526, though the invention is not limited thereto. In other embodiments, configuration of the first light source 110, the second light source 210, the first pupil image capturing device 120, the second pupil image capturing device 220, the first environmental image capturing device 130 and the second environmental image capturing device 140 can be determined according to an actual design requirement. For example, the second light source 210 can be disposed on at least one of the first connection portion 1523, the second connection portion 1524 adjacent to the second eye E2 and the ear hooking portion 1526 adjacent to the second eye E2. Moreover, the second light source 210 and the first light source 110 can be symmetrically or asymmetrically disposed on the fixing device 150, the first pupil image capturing device 120 and the second pupil image capturing device 220 can be symmetrically or asymmetrically disposed on the fixing device 150, and the first environmental image capturing device 130 and the second environmental image capturing device 140 can also be symmetrically or asymmetrically disposed on the fixing device 150.

The second light source 210 sends a second light beam L21 to illuminate the second eye E2 of the user. The second light source 210 can be a visible-light light source or an invisible-light light source. Particularly, when the invisible-light light source is used as the second light source 210, visibility of the second light beam L21 sent by the second light source 210 is decreased. Moreover, when the second light source 210 also adopts the IR LED the same with that of the first light source 110, by forming IR filters on surfaces of the lenses 154a and 154b adjacent to the user, contrasts of the first pupil image and the second pupil image are further improved.

The second pupil image capturing device 220 is applied for capturing a second pupil image of the second eye E2 and is, for example, disposed at a position that is suitable for directly or indirectly capture the second pupil image. For example, the second pupil image capturing device 220 can be disposed on the second connection portion 1524 or the first connection portion 1523 and face the second eye E2. Alternatively, as shown in FIG. 2, the second pupil image capturing device 220 can also be disposed on a transmission path of the second light beam L22 reflected by the second eye E2 to capture the second pupil image of the second eye E2. In the present embodiment, the second light beam L22 reflected by the second eye E2 is, for example, reflected at least once by the lens 154a and is transmitted to the second pupil image capturing device 220. Namely, the second pupil image capturing device 220 is, for example, disposed on a transmission path of the second light beam L23 reflected by the lens 154a. Since the second pupil image capturing device 220 is fixed around the second eye E2 of the user (for example, fixed on the ear hooking portion 1526) instead of disposing the same in front of the user, the problem of shielding a sight line is mitigated. Moreover, by transmitting the second pupil image to the second pupil image capturing device 220 through reflection of the lens 154a, an angle that the first pupil image is obliquely incident to the second pupil image capturing device 220 is decreased, so as to decrease a calibration error and improve a resolution.

The second pupil image capturing device 220 can be a charge-coupled device, a complementary metal oxide semiconductor device or an IR camera, wherein the second pupil image capturing device 220 has a horizontal viewing angle and a vertical viewing angle. Since a field of vision of human eye is rather broad, in order to accurately obtain the second pupil image of the second eye E2, the horizontal viewing angle of the second pupil image capturing device 220 of the present embodiment is greater than 40 degrees and smaller than 180 degrees, and the vertical viewing angle is greater than 55 degrees and smaller than 180 degrees.

In the present embodiment, the second pupil image can be transmitted to the image identification system 160 through a wired or wireless transmission manner. Moreover, the image identification system 160 is adapted to map at least one of the first environmental image and the second environmental image to the second pupil image, so as to determine the gazing position of the user. In detail, the first pupil image and the second pupil image can be mapped to at least one of the first environmental image and the second environmental image.

Moreover, the head-mount eye tracking system 200 may further include the data storage system 170 and the transmission element 180, wherein the transmission element 180 can transmit the first pupil image, the second pupil image, the first environmental image and the second environmental image or the gazing position of the user identified after the mapping to the data storage system 170, and the transmission method and applications of the above elements may refer to the aforementioned related descriptions, and details thereof are not repeated.

The head-mount eye tracking system 200 of the present embodiment tracks the eyes (the first eye E1 and the second eye E2) through the non-invasive manner (i.e. the head-mount eye tracking system 200 does not directly contact the eye), and the first and the second environmental image capturing devices 130 and 140 are used to capture the environmental images in front of the user, and the image identification system 160 is used to map at least one of the first environmental image and the second environmental image to the first pupil image and the second pupil image, so as to identify the gazing position of the user. Since the head-mount eye tracking system 200 of the present embodiment can mitigate problems of wrong determination and shielding of the sight line, and can improve determination accuracy by obtaining distance information between the user and the object in the environment (i.e. a distance of the object), the head-mount eye tracking system 200 of the present embodiment has a broad application range. For example, when the head-mount eye tracking system 200 of the present embodiment is used in collaboration with computer mouse operation, a convenient eye tracking and controlling system is provided to people with disabilities or people with inconvenient hands. On the other hand, the head-mount eye tracking system 200 of the present embodiment can also objectively analyze consumer psychology and market trends or provide driving warnings by identifying eye tracks. Moreover, by combining a brain wave measurement, the head-mount eye tracking system 200 of the present embodiment can further determine an influence of user's physical or mental illness on the eye track or concentration.

In summary, in the head-mount eye tracking system of the invention, by configuring the environmental image capturing devices and the pupil image capturing devices to capture the environmental images in front of the user and the pupil images of the eyes, and by mapping the environmental image to the pupil image, the problem of wrong determination is mitigated. Moreover, by configuring two environmental image capturing devices, the head-mount eye tracking system of the invention may further obtain distance information (i.e. a distance of an object) between the object in the environment and the user, so as to improve determination accuracy. Furthermore, the head-mount tracking system of the invention fixes the light source and the image capturing device around the eye of the user instead of disposing the same in front of the user, so as to mitigate the problem of shielding the sight line.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A head-mount eye tracking system, comprising:
    a first light source, sending a first light beam to illuminate a first eye of a user;
    a first pupil image capturing device, disposed on a transmission path of the first light beam reflected by the first eye to capture a first pupil image of the first eye;
    a first environmental image capturing device, adapted to capture a first environmental image in front of the user;
    a second environmental image capturing device, adapted to capture a second environmental image in front of the user;
    a fixing device, disposed on the head of the user for fixing the first light source, the first pupil image capturing device, the first environmental image capturing device and the second environmental image capturing device on the head of the user; and
    an image identification system, adapted to map at least one of the first environmental image and the second environmental image to the first pupil image, so as to determine a gazing position of the user, wherein the fixing device is a pair of glasses, the pair of glasses comprises a glasses frame and two lenses fixed on the glasses frame, the glasses frame comprises two lens frame portions, a first connection portion, two second connection portions and two ear hooking portions, wherein the first connection portion connects the two lens frame portions, each of the second connection portions connects the ear hooking portion with the adjacent lens frame portion, and the lenses are located in the lens frame portions, the first environmental image capturing device and the second environmental image capturing device are disposed on the first connection portion, and the first pupil image capturing device is disposed on the ear hooking portion adjacent to the first eye, and the first light source is disposed on one of the first connection portion, the second connection portion adjacent to the first eye and the ear hooking portion adjacent to the first eye.

2. The head-mount eye tracking system as claimed in claim 1, wherein the first light source is selected from a visible-light light source or an invisible-light light source.

3. The head-mount eye tracking system as claimed in claim 2, wherein the invisible-light light source is selected from an infrared light-emitting diode (IR LED), an ultraviolet light-emitting diode (UV LED) or laser.

4. The head-mount eye tracking system as claimed in claim 1, wherein the first pupil image capturing device, the first environmental image capturing device and the second environmental image capturing device are respectively selected from a charge coupled device (CCD), a complementary metal-oxide semiconductor (CMOS) device or an infrared (IR) camera.

5. The head-mount eye tracking system as claimed in claim 1, further comprising:
    a second light source, sending a second light beam to illuminate a second eye of the user; and
    a second pupil image capturing device, disposed on a transmission path of the second beam reflected by the second eye to capture a second pupil image of the second eye, wherein the second light source and the second pupil image capturing device are fixed on the fixing device, and the image identification system is adapted to map at least one of the first environmental image and the second environmental image to the second pupil image.

6. The head-mount eye tracking system as claimed in claim 1, further comprising:
    a data storage system, adapted to store the first pupil image, the first environmental image and the second environmental image, or store the gazing position of the user that is identified by the image identification system; and
    a transmission element, wherein the gazing position of the user that is identified by the image identification system or the first pupil image, the first environmental image and the second environmental image are transmitted to the data storage system through the transmission element.

* * * * *